United States Patent
Gege

(10) Patent No.: US 9,932,332 B2
(45) Date of Patent: Apr. 3, 2018

(54) FXR (NR1H4) MODULATING COMPOUNDS

(71) Applicant: Gilead Sciences, Inc., Foster City, CA (US)

(72) Inventor: Christian Gege, Mauer (DE)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/619,883

(22) Filed: Jun. 12, 2017

(65) Prior Publication Data

US 2017/0355694 A1    Dec. 14, 2017

Related U.S. Application Data

(60) Provisional application No. 62/349,494, filed on Jun. 13, 2016.

(51) Int. Cl.
*C07D 493/08* (2006.01)
*C07D 417/14* (2006.01)

(52) U.S. Cl.
CPC ......... *C07D 417/14* (2013.01); *C07D 493/08* (2013.01)

(58) Field of Classification Search
CPC .................... C07D 417/14; C07D 493/08
See application file for complete search history.

(56) References Cited

FOREIGN PATENT DOCUMENTS

WO    WO-2011/020615 A1    2/2011
WO    WO-2016/096115 A1 *  6/2016

OTHER PUBLICATIONS

Ali, et al., (2015), Recent advances in the development of farnesoid X receptor agonists, Annl Transl Med., 3:5 (16pgs).
Written Opinion and ISR for PCT/US2017/036955, dated Sep. 6, 2017, 9pgs.

* cited by examiner

*Primary Examiner* — Laura L Stockton

(57) ABSTRACT

The present disclosure relates generally to compounds which bind to the NR1H4 receptor (FXR) and act as agonists of FXR. The disclosure further relates to the use of the compounds for the preparation of a medicament for the treatment of diseases and/or conditions through binding of said nuclear receptor by said compounds and to a process for the synthesis of said compounds.

6 Claims, No Drawings

SEQUENCE LISTING

<160> NUMBER OF SEQ ID NOS: 1

<210> SEQ ID NO 1
<211> LENGTH: 25
<212> TYPE: PRT
<213> ORGANISM: Artificial Sequence
<220> FEATURE:

```
<223> OTHER INFORMATION: Synthetic

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

FXR (NR1H4) MODULATING COMPOUNDS

CROSS REFERENCE TO RELATED APPLICATIONS

This application claims the benefit of U.S. Provisional App. No. 62/349,494, filed Jun. 13, 2016, the entirety of which is hereby incorporated by reference.

SEQUENCE LISTING

The Sequence Listing associated with this application is provided in text format in lieu of a paper copy, and is hereby incorporated by reference into the specification. The name of the text file containing the Sequence Listing is 1172_PC_ST25.txt. The text file created on May 16, 2017, is about 550 bytes and submitted electronically via EFS-Web.

FIELD

The present disclosure relates to compounds which bind to the NR1H4 receptor (FXR) and act as agonists or modulators of FXR. The disclosure further relates to the use of the compounds for the treatment and/or prophylaxis of diseases and/or conditions through binding of said nuclear receptor by said compounds.

BACKGROUND

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR." Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface.

In general, three functional domains have been defined in NRs. An amino terminal domain is believed to have some regulatory function. It is followed by a DNA-binding domain (hereinafter referred to as "DBD"), which usually comprises two zinc finger elements and recognizes a specific Hormone Responsive Element (hereinafter referred to as "HRE") within the promoters of responsive genes. Specific amino acid residues in the "DBD" have been shown to confer DNA sequence binding specificity. A ligand-binding-domain (hereinafter referred to as "LBD") is at the carboxy-terminal region of known NRs.

In the absence of hormone, the LBD appears to interfere with the interaction of the DBD with its HRE. Hormone binding seems to result in a conformational change in the NR and thus opens this interference. A NR without the LBD constitutively activates transcription but at a low level.

Coactivators or transcriptional activators are proposed to bridge between sequence specific transcription factors, and the basal transcription machinery and in addition to influence the chromatin structure of a target cell. Several proteins like SRC-1, ACTR, and Grip 1 interact with NRs in a ligand enhanced manner.

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression.

The Farnesoid X Receptor alpha (hereinafter also often referred to as NR1H4 when referring to the human receptor) is a prototypical type 2 nuclear receptor which activates genes upon binding to a promoter region of target genes in a heterodimeric fashion with Retinoid X Receptor. The relevant physiological ligands of NR1H4 are bile acids. The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents) or 19 (monkeys, humans A).

Although numerous FXR agonists are known, there is a need for improved FXR agonists.

SUMMARY

The present disclosure provides compounds bind to the NR1H4 receptor (FXR) and act as agonists or modulators of FXR. The disclosure further relates to the use of the compounds for the treatment and/or prophylaxis of diseases and/or conditions through binding of said nuclear receptor by said compounds.

The present disclosure provides compounds selected from:

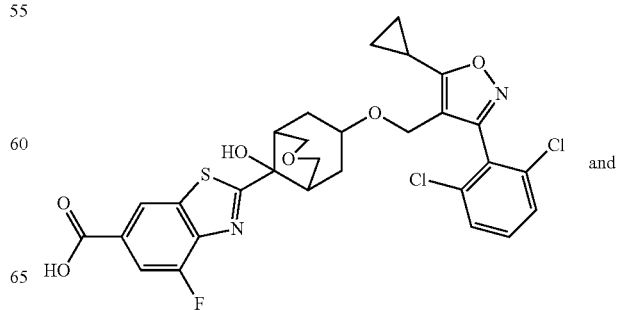

and

-continued

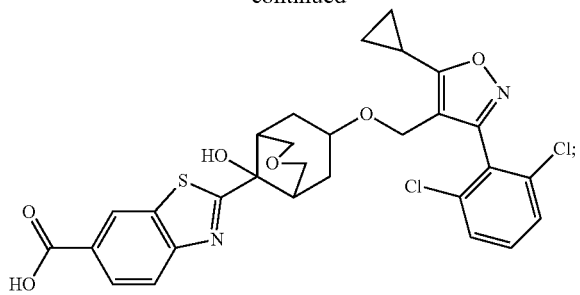

or a pharmaceutically acceptable salt, a stereoisomer, a mixture of stereoisomers, or a tautomer thereof.

Some embodiments provide for pharmaceutical compositions comprising a compound disclosed herein and a pharmaceutically acceptable excipient.

Also provided herein are methods of treating a patient having an FXR mediated condition comprising administering a compound disclosed herein to a patient in need thereof.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Furthermore, the compounds of the present disclosure may be subject to tautomerism. Where tautomerism, e.g. keto-enol tautomerism, of compounds of the present disclosure or their prodrugs may occur, the individual forms, like e.g. the keto and enol form, are each within the scope of the disclosure as well as their mixtures in any ratio. The same applies for stereoisomers, like e.g. enantiomers, cis/trans isomers, conformers and the like.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

In some embodiments, the compounds of the present disclosure can be in the form of a "prodrug." The term "prodrug" is defined in the pharmaceutical field as a biologically inactive derivative of a drug that upon administration to the human body is converted to the biologically active parent drug according to some chemical or enzymatic pathway. Examples of prodrugs include esterified carboxylic acids.

In the human liver, UDP-glucuronosyltransferases act on certain compounds having amino, carbamyl, thio (sulfhydryl) or hydroxyl groups to conjugate uridine diphosphate-α-D-glucuronic acid through glycoside bonds, or to esterify compounds with carboxy or hydroxyl groups in the process of phase II metabolism. Compounds of the present disclosure may be glucuronidated, that is to say, conjugated to glucuronic acid, to form glucuronides, particularly (β-D) glucuronides.

One step in the formation of bile is the conjugation of the individual bile acids with an amino acid, particularly glycine or taurine. Compounds of the present disclosure may be conjugated with glycine or taurine at a substitutable position.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present disclosure which contain one or more basic groups, i.e. groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g. by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another. "Diastereomers" are stereoisomers that have at least two asymmetric atoms, but which are not mirror-images of each other.

The compounds disclosed herein and their pharmaceutically acceptable salts may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula I when administered to a mammal, e.g. a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor.

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing at least one compound of the present disclosure and a pharmaceutically acceptable carrier.

| List of Abbreviations and Acronyms | |
|---|---|
| Abbreviation | Meaning |
| AcOH | Acetic acid |
| BSA | Bovine serum albumin |
| BSS | Balanced Salt Solution |
| DCM | Dichloromethane |
| DMF | Dimethylformamide |
| DMSO | Dimethylsulfoxide |
| EDTA | Ethylenediaminetetraacetic acid |
| ESI | Electronspray Ionization |
| EtOAc | Ethyl acetate |
| EtOH | Ethanol |
| FBS | Fetal bovine serum |
| h or hr(s) | Hour(s) |
| IPTG | Isopropyl β-D-1-thiogalactopyranoside |
| LCMS | Liquid Chromatography Mass Spectrometry |
| MEM | Minimum Essential Medium |
| MeOH | Methanol |
| min | Minute(s) |

| List of Abbreviations and Acronyms | |
|---|---|
| Abbreviation | Meaning |
| MS | Mass Spectrometry |
| NMR | Nuclear Magnetic Resonance spectroscopy |
| n-BuLi | n-butyllithium |
| rpm | Revolutions per minute |
| RT or rt | Room temperature |
| THF | tetrahydrofuran |

Compounds

Provided herein are compounds selected from:

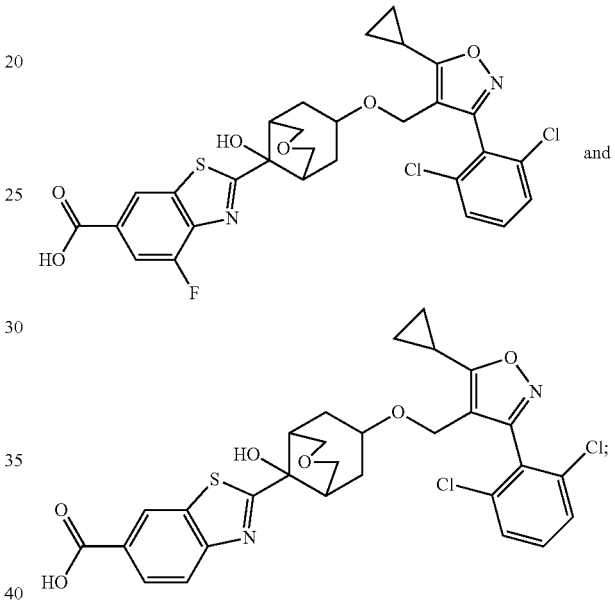

or a pharmaceutically acceptable salt, a stereoisomer, a mixture of stereoisomers, or a tautomer thereof.

The chemical name of each of these compounds is provided in Table 1 below.

TABLE 1

| Example | Structure | IUPAC Name |
|---|---|---|
| 1 | 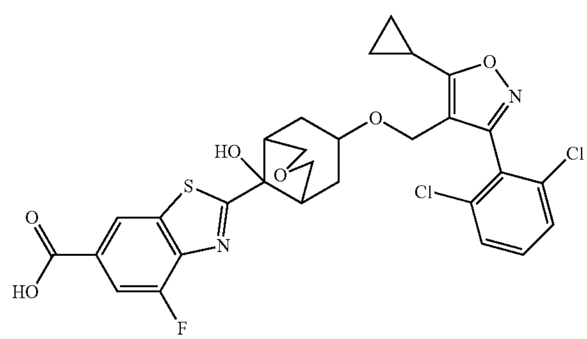 [SMILES: O=C(O)c1cc(F)c2nc(C3(O)C4COCC3CC(OCc3c(-c5c(Cl)cccc5Cl)noc3C3CC3)C4)sc2c1] | 2-(7-((5-cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carboxylic acid |

TABLE 1-continued

| Example | Structure | IUPAC Name |
|---|---|---|
| 2 | 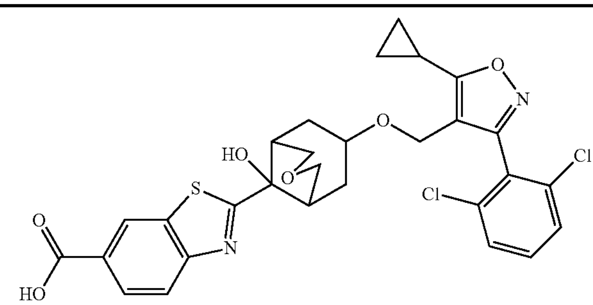 | 2-(7-((5-cyclopropyl-3-(2,6-dichlorophenyl)isoxazol-4-yl)methoxy)-9-hydroxy-3-oxabicyclo[3.3.1]nonan-9-yl)benzo[d]thiazole-6-carboxylic acid |

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other nuclear receptor modulators.

Pharmaceutical compositions may be suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since salt forms of ionic compounds can substantially affect bioavailability, the compounds of the present disclosure may also be used as salts with various counterions to yield an orally available formulation. Pharmaceutically acceptable counterions may be mono- or bivalent ions such as ammonium, the alkaline metals sodium or potassium or the alkaline earth metals magnesium or calcium, certain pharmaceutically acceptable amines such as tris(hydroxymethyl)aminomethane, ethylendiamine, diethylamine, piperazine or others, or certain cationic amino acids such as lysine or arginine.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "prophylaxis" refers to the treatment of a disease or condition that causes the clinical symptoms of the disease or condition not to develop or progress. Compounds may, in some embodiments, be administered to a subject (including a human) who is at risk or has a family history of the disease or condition in order to prevent the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The disclosure further relates to the use of said compounds for the treatment and/or prophylaxis of diseases and/or conditions through binding of said nuclear receptor by said compounds. Further the present disclosure relates to the use of said compounds for the preparation of a medicament for the treatment and/or prophylaxis of diseases and/or conditions through binding of said nuclear receptor by said compounds.

Specifically, the present disclosure relates to the use of compounds disclosed herein in the preparation of a medicament for the prophylaxis and/or treatment of chronic intrahepatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present disclosure and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestosis and many other diseases.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or CDCA, this can be regarded as an example of feedback inhibition on the gene expression level. Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice. where under- or overexpression of several ABC-transporters in the liver was shown. Further detailed analysis revealed that the major bile salt excretory pump BSEP or ABCB11 (as well as the key enzyme which mediates lipid transfer from lipoproteins to phospholipids, PLTP, and the two key canalicular membrane transporters for phospholipids, MRP-2 (ABCC4) and MDR-3 (ABCB4), are direct targets for ligand-directed transcriptional activation by FXR.

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated. This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 in hepatic stellate cells and the subsequent reduction of alpha-collagen mRNA and Transforming growth factor beta (TGF-beta) mRNA which are both pro-fibrotic factors by FXR agonists. Furthermore, anti-cholestatic activity was demonstrated in bile-duct ligated animal models as well as in animal models of estrogen-induced cholestasis.

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC 1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease. Using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation.

These results qualify FXR as a good target for the development of small molecule agonists that can be used to prevent cholesterol gallstone formation or to prevent re-formation of gallstones after surgical removal or shockwave lithotripsy.

Thus, in one embodiment of the disclosure, the compounds disclosed herein and pharmaceutical compositions comprising said compounds are used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut. Similar to the situation in the intestine absence of FXR leads to a high increase in the formation of Hepatocellular Cacrcinoma (HCC), the most prominent form of liver cancer. Whereas a functional FXR prevents the formation of colon adenocarcinoma and hepatocellular carcinoma, FXR activation induces liver regeneration after hepatectomy.

The combined hepatoprotective, anti-neoplastic and liver regenerative effects associated with FXR activation can be therapeutically exploited for the use of FXR agonists in the treatment of severe liver diseases. In one embodiment, the compounds according to the disclosure and pharmaceutical compositions comprising said compounds are used in the treatment of liver diseases such as HCC, stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides. Over the past six years accumulating evidence has been published that activation of FXR by synthetic agonists leads to significant reduction of serum triglycerides, mainly in the form of reduced VLDL, but also to reduced total serum cholesterol.

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment. An effect on reduction of body weight was also recently observed in mice overfed with a high lipid diet. This weight loss effect might results from FXR's induction of FGF-19, a fibroblast growth factor that is known to lead to weight loss and athletic phenotype. The effect of FXR agonist on reduction of body weight has been demonstrated.

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the disclosure and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as PBC, PSC, progressive familiar cholestasis (PFIC), alcohol-induced cirrhosis and associated cholestasis, and some forms of extrahepatic cholestatic conditions, or liver fibrosis.

The disclosure also relates to a compound disclosed herein or a pharmaceutical composition comprising a compound disclosed herein for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as Non-Alcoholic Steatohepatitis (NASH), or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice. Therefore, FXR agonists might have clinical utility as anti-atherosclerotic and cardioprotective drugs. The downregulation of Endothelin-1 in Vascular Smooth Muscle Cells might also contribute to such beneficial therapeutic effects.

The disclosure also relates to a compound disclosed herein or a pharmaceutical composition comprising a compound disclosed herein for preventive and posttraumatic treatment of a cardiovascular disorder, such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells.

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer where interference with an FXR ligand will have a beneficial impact.

Finally, FXR seems also to be involved in the control of antibacterial defense in the intestine although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD, the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the disclosure also relates to a compound disclosed herein or a pharmaceutical composition comprising said compounds for preventing and/or treating a disease related to an Inflammatory Bowel Disease, such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The disclosure further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In a further embodiment, the compounds or pharmaceutical composition of the present disclosure are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present disclosure.

Furthermore, conditions and diseases which result from chronic fatty and fibrotic degeneration of organs due to enforced lipid and specifically triglyceride accumulation and subsequent activation of profibrotic pathways may also be prevented and/or treated by administering the compounds or pharmaceutical composition of the present disclosure. Such conditions and diseases encompass NASH and chronic cholestatic conditions in the liver, Glomerulosclerosis and Diabetic Nephropathy in the kidney, Macula Degeneration and Diabetic Retinopathy in the eye and neurodegenerative diseases, such as Alzheimer's Disease in the brain, or Diabetic Neuropathies in the peripheral nervous system.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present disclosure are indicated, generally satisfactory results are obtained when the compounds of the present disclosure are administered at a daily dosage of from about 0.1 milligram to about 100 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 7 milligrams to about 350 milligrams. This dosage regimen may be adjusted to provide the optimal therapeutic response. In some embodiments, the total daily dosage is from about 1 milligram to about 900 milligrams, about 10 milligrams to about 800 milligrams, about 20 milligrams to about 700 milligrams, about 30 milligrams to about 600 milligrams, about 40 milligrams to about 550 milligrams, or about 50 milligrams to about 400 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combination Therapies

In some embodiments, a compound disclosed herein is administered in combination with one or more additional therapeutic agents to treat or prevent a disease or condition disclosed herein. In some embodiments, the one or more additional therapeutic agents are a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21(miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor 3 (TGF-β3), Transforming growth factor β activated Kinase 1 (TAKi), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator.

Non-limiting examples of the one or more additional therapeutic agents include:

ACE inhibitors, such as enalapril;

Acetyl CoA carboxylase (ACC) inhibitors, such as NDI-010976, DRM-01, gemcabene, PF-05175157, and QLT-091382;

Adenosine receptor agonists, such as CF-102, CF-101, CF-502, and CGS21680;

Adiponectin receptor agonists, such as ADP-355;

Amylin/calcitonin receptor agonists, such as KBP-042;

AMP activated protein kinase stimulators, such as O-304;

Angiotensin II AT-1 receptor antagonists, such as irbesartan;

Autotaxin inhibitors, such as PAT-505, PAT-048, GLPG-1690, X-165, PF-8380, and AM-063;

Bioactive lipids, such as DS-102;

Cannabinoid receptor type 1 (CNR1) inhibitors, such as namacizumab and GWP-42004;

Caspase inhibitors, such as emricasan;

Pan cathepsin B inhibitors, such as VBY-376;

Pan cathepsin inhibitors, such as VBY-825;

CCR2/CCR5 chemokine antagonists, such as cenicriviroc;

CCR2 chemokine antagonists, such as propagermanium;

CCR3 chemokine antagonists, such as bertilimumab;

Chloride channel stimulators, such as cobiprostone;

Diglyceride acyltransferase 2 (DGAT2) inhibitors, such as IONIS-DGAT2Rx;

Dipeptidyl peptidase IV inhibitors, such as linagliptin;

Eotaxin ligand inhibitors, such as bertilimumab;

Extracellular matrix protein modulators, such as CNX-024;

Farnesoid X receptor (FXR) agonists, such as AGN-242266, AKN-083, EDP-305, GNF-5120, GS-9674, LJN-452, LMB-763, obeticholic acid, Px-102, Px-103, M790, M780, M450, M480, PX20606, EYP-001, and INT-2228;

Farnesoid X receptor (FXR)/G-protein coupled bile acid receptor 1(TGR5) agonists, such as INT-767;

Fatty acid synthase inhibitors, such as TVB-2640;

Fibroblast growth factor 19 (rhFGF19)/cytochrome P450 (CYP)7A1 inhibitors, such as NGM-282;

Fibroblast growth factor 21(FGF-21) ligand, such as BMS-986171, BMS-986036;

Fibroblast growth factor 21(FGF-21)/glucagon like peptide 1 (GLP-1) agonists, such as YH-25723;

Galectin-3 inhibitors, such as GR-MD-02;

Glucagon-like peptide 1(GLP1R) agonists, such as AC-3174, liraglutide, semaglutide;

G-protein coupled bile acid receptor 1(TGR5) agonists, such as RDX-009, INT-777;

Heat shock protein 47 (HSP47) inhibitors, such as ND-L02-s0201;

HMG CoA reductase inhibitors, such as atorvastatin, fluvastatin, pitavastatin, pravastatin, rosuvastatin, and simvastatin;

IL-10 agonists, such as peg-ilodecakin;

Ileal sodium bile acid cotransporter inhibitors, such as A-4250, volixibat potassium ethanolate hydrate (SHP-262), and GSK2330672;

Insulin sensitizers, such as, KBP-042, MSDC-0602K, Px-102, RG-125 (AZD4076), and VVP-100X;

beta Klotho (KLB)-FGFlc agonist, such as NGM-313;

5-Lipoxygenase inhibitors, such as tipelukast (MN-001);

Lipoprotein lipase inhibitors, such as CAT-2003;

LPL gene stimulators, such as alipogene tiparvovec;

Liver X receptor (LXR) modulators, such as PX-L603, PX-L493, BMS-852927, T-0901317, GW-3965, and SR-9238;

Lysophosphatidate-1 receptor antagonists, such as BMT-053011, UD-009. AR-479, ITMN-10534, BMS-986020, and KI-16198;

Lysyl oxidase homolog 2 inhibitors, such as simtuzumab;

MEKK-5 protein kinase inhibitors, such as GS-4997;

Semicarbazide-Sensitive Amine Oxidase/Vascular Adhesion Protein-1 (SSAO/VAP-1) Inhibitors, such as PXS-4728A;

Methionine aminopeptidase-2 inhibitors, such as ZGN-839;

Methyl CpG binding protein 2 modulators, such as mercaptamine;

Mitochondrial uncouplers, such as 2,4-dinitrophenol;

Myelin basic protein stimulators, such as olesoxime;

NADPH oxidase 1/4 inhibitors, such as GKT-831;

Nicotinic acid receptor 1 agonists, such as ARI-3037MO;

NACHT LRR PYD domain protein 3 (NLRP3) inhibitors, such as KDDF-201406-03, and NBC-6;

Nuclear receptor modulators, such as DUR-928;

P2Y13 purinoceptor stimulators, such as CER-209;

PDE 3/4 inhibitors, such as tipelukast (MN-001);

PDE 5 inhibitors, such as sildenafil;

PDGF receptor beta modulators, such as BOT-191, BOT-509;

PPAR agonists, such as elafibranor (GFT-505), MBX-8025, deuterated pioglitazone R-enantiomer, pioglitazone, DRX-065, saroglitazar, and IVA-337;

Protease-activated receptor-2 antagonists, such as PZ-235;

Protein kinase modulators, such as CNX-014;

Rho associated protein kinase (ROCK) inhibitors, such as KD-025;

Sodium glucose transporter-2(SGLT2) inhibitors, such as ipragliflozin, remogliflozin etabonate, ertugliflozin, dapagliflozin, and sotagliflozin;

SREBP transcription factor inhibitors, such as CAT-2003 and MDV-4463;

Stearoyl CoA desaturase-1 inhibitors, such as aramchol;

Thyroid hormone receptor beta agonists, such as MGL-3196, MGL-3745, VK-2809;

TLR-4 antagonists, such as JKB-121;

Tyrosine kinase receptor modulators, such as CNX-025;

GPCR modulators, such as CNX-023; and

Nuclear hormone receptor modulators, such as Px-102.

In certain specific embodiments, the one or more additional therapeutic agents are selected from A-4250, AC-3174, acetylsalicylic acid, AK-20, alipogene tiparvovec, aramchol, ARI-3037MO, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GR-MD-02, GS-4997, GS-9674, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, NDI-010976, ND-L02-s0201, NGM-282, NGM-313, NGM-386, NGM-395, norursodeoxycholic acid, 0-304, obeticholic acid, 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, and ZGN-839.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

The compounds of the present disclosure can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared.

The compounds illustrated in the examples are not, however, to be construed as forming the only genus that is considered as the disclosure. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. The instant compounds are generally isolated in the form of their pharmaceutically acceptable salts, such as those described above. In general, compounds described herein are typically stable and isolatable at room temperature and pressure The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present disclosure is shown below. Unless otherwise indicated in the schemes, the variables have the same meaning as described above. The examples presented below are intended to illustrate particular embodiments of the disclosure. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Synthesis 1

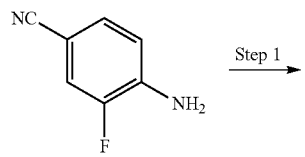

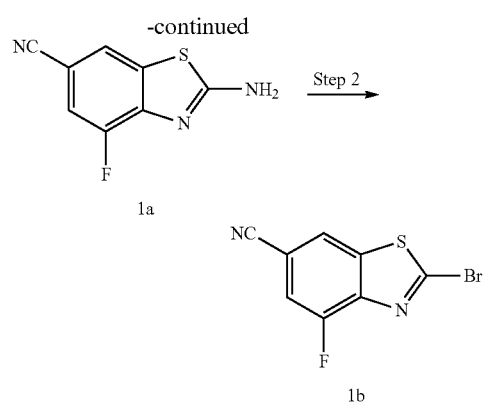

Step 1: 2-Amino-4-fluorobenzo[d]thiazole-6-carbonitrile (1a)

To a stirred solution of 4-amino-3-fluorobenzonitrile (2.0 g, 14.7 mmol) and potassium thiocyanide (5.7 g, 59 mmol) in AcOH (50 mL) was added a solution of bromine (2.3 g, 14.7 mmol) in AcOH (5 mL) over 20 min. The mixture was stirred at rt for 20 h, poured into ice-water (100 mL). Ammonium hydroxide solution (28%) was added to pH 8, the mixture was stirred for 2 h, filtered, washed with water and dried to afford 2-amino-4-fluorobenzo[d]thiazole-6-carbonitrile (1a).

Step 2: 2-Bromo-4-fluorobenzo[d]thiazole-6-carbonitrile (1b)

A solution of 2-amino-4-fluorobenzo[d]thiazole-6-carbonitrile (1a, 2.0 g, 10 mmol), tert-BuONO (1.5 g, 15 mmol) and CuBr$_2$ (3.3 g, 15 mmol) in MeCN (100 mL) was stirred at rt overnight, quenched with water (100 mL) and extracted with EtOAc (3×100 mL). The combined organic layer was dried over Na$_2$SO$_4$, filtered and concentrated to afford 2-bromo-4-fluorobenzo[d]thiazole-6-carbonitrile (1b).

General Synthesis 2

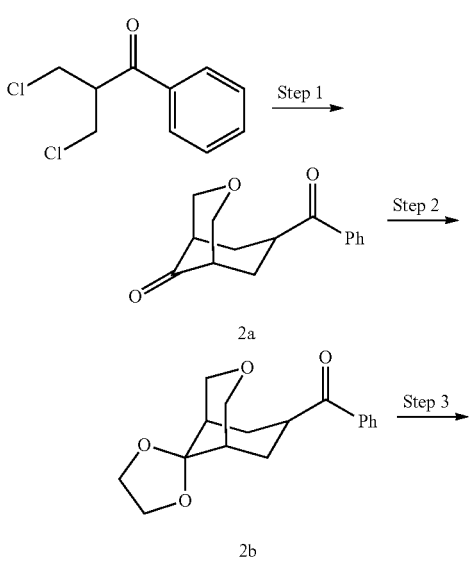

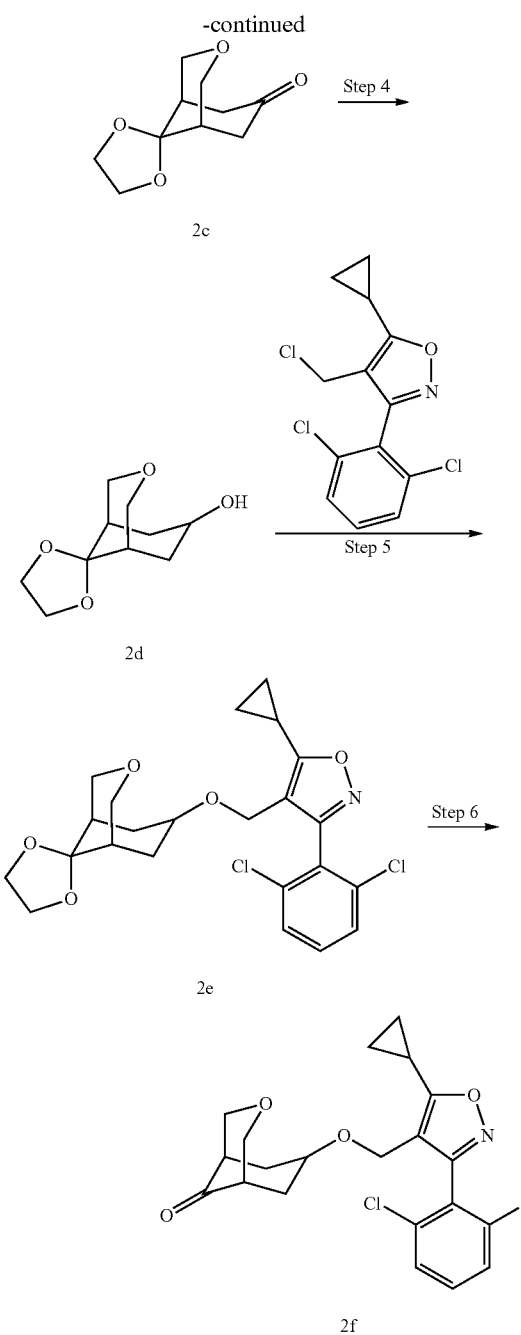

Step 2: Phenyl((1R,5S)-3-oxaspiro[bicyclo[3.3.1] nonane-9,2'-[1,3]dioxolan]-7-yl)methanone (2b)

A solution of (1R,5S)-7-benzoyl-3-oxabicyclo[3.3.1] nonan-9-one (7.8 g, 32.0 mmol), ethane-1,2-diol (2.4 g, 38.4 mmol) and p-TsOH (500 mg) in toluene (100 mL) was heated to reflux overnight, poured into NaHCO$_3$ (aq.) and extracted with EtOAc (3×100 mL). The organic layers were combined, dried over Na$_2$SO$_4$, concentrated and purified by column chromatography to give phenyl((1R,5S)-3-oxaspiro [bicyclo[3.3.1]nonane-9,2'-[1,3]dioxolan]-7-yl)methanone (2b).

Step 3: (1R,5S)-3-oxaspiro[bicyclo[3.3.1]nonane-9, 2'-[1,3]dioxolan]-7-one (2c)

To a mixture of phenyl((1R,5S)-3-oxaspiro[bicyclo[3.3.1] nonane-9,2'-[1,3]dioxolan]-7-yl)methanone (7.5 g, 26.0 mmol), potassium tert-butoxide (3.4 g, 30.0 mmol) and tert-butyl alcohol (100 mL) was added hexamethylphosphoric triamide (100 mL). The mixture was saturated with O$_2$ while stirring at 55° C. After the reaction was complete (determined by TLC), water (1 L) was added and the mixture was extracted with EtOAc (3×100 mL). The organic layers were combined, washed with water (2×100 mL), dried over Na$_2$SO$_4$, concentrated and purified by column chromatography to give (1R,5S)-3-oxaspiro[bicyclo[3.3.1]nonane-9, 2'-[1,3]dioxolan]-7-one (2c). $^1$H-NMR (500 MHz, CDCl$_3$) δ 4.09-4.04 (m, 4H), 3.89 (d, J=11.0 Hz, 2H), 3.78 (d, J=11.0 Hz, 2H), 2.84 (dd, J=16.0 Hz, J=5.0 Hz, 2H), 2.40 (d, J=16.0 Hz, 2H), 2.00 (d, J=5.0 Hz, 2H).

Step 4: (1R,5S)-3-Oxaspiro[bicyclo[3.3.1]nonane-9, 2'-[1,3]dioxolan]-7-ol (2d)

To a mixture of (1R,5S)-3-oxaspiro[bicyclo[3.3.1] nonane-9,2'-[1,3]dioxolan]-7-one (1.0 g, 5.0 mmol) in MeOH/DCM (10 mL/40 mL) was added NaBH$_4$ (760 mg, 20.0 mmol) in several portions at 0° C. The mixture was stirred at rt overnight, poured into a NH$_4$Cl solution and extracted with EtOAc (3×50 mL). The organic layers were combined, dried over Na$_2$SO$_4$ and concentrated to give (1R,5S)-3-oxaspiro[bicyclo[3.3.1]nonane-9,2'-[1,3]dioxolan]-7-ol, which was used in the next step without further purification.

Step 5: 4-(((1R,5S)-3-Oxaspiro[bicyclo[3.3.1] nonane-9,2'-[1,3]dioxolan]-7-yloxy)methyl)-5-cyclopropyl-3-(2,6-dichlorophenyl)isoxazole (2e)

To a suspension of NaH (60% in mineral oil) (580 mg, 14.4 mmol) in THF (30 mL) was added (1R,5S)-3-oxaspiro [bicyclo[3.3.1]nonane-9,2'-[1,3]dioxolan]-7-ol (570 mg, 2.88 mmol) in THF (10 mL) at 0° C. The reaction mixture was stirred at 0° C. for 1.5 h, then 4-(chloromethyl)-5-cyclopropyl-3-(2,6-dichlorophenyl)isoxazole (prepared according to procedures set forth in International Application Publication No. WO 2011/020615) (1.2 g, 3.46 mmol) was added at 0° C. and stirred at reflux overnight. The reaction was quenched with NH$_4$Cl (sat.) and extracted with EtOAc (3×20 mL). The organic layers were combined, washed with brine (2×20 mL), dried over Na$_2$SO$_4$, concentrated and purified by chromatography to give 4-(((1R,5S)-3-oxaspiro[bicyclo[3.3.1]nonane-9,2'-[1,3]dioxolan]-7-yloxy)methyl)-5-cyclopropyl-3-(2,6-dichlorophenyl) isoxazole (2e).

Step 1: (1R,5S)-7-benzoyl-3-oxabicyclo[3.3.1] nonan-9-one (2a)

A solution of 3-chloro-2-(chloromethyl)-1-phenylpropan-1-one (10 g, 45.8 mmol), 1-(3,6-dihydro-2H-pyran-4-yl) pyrrolidine (7.0 g, 45.8 mmol) and triethylamine (5.0 g, 50.0 mmol) in CH$_3$CN (150 mL) was heated to reflux for 1 h, cooled to rt, diluted with water (150 mL) and stirred at rt overnight. The mixture was extracted with EtOAc (3×100 mL). The organic layers were combined, dried over Na$_2$SO$_4$, concentrated and purified by column chromatography to give (1R,5S)-7-benzoyl-3-oxabicyclo[3.3.1]nonan-9-one (2a).

Step 6: (1R,5S)-7-((5-Cyclopropyl-3-(2,6-dichlorophenyl)isoxazol-4-yl)methoxy)-3-oxabicyclo[3.3.1]nonan-9-one (2f)

To a stirred solution of 4-(((1R,5S)-3-oxaspiro[bicyclo[3.3.1]nonane-9,2'-[1,3]dioxolan]-7-yloxy)methyl)-5-cyclopropyl-3-(2,6-dichlorophenyl)isoxazole (160 mg, 0.34 mmol) in acetone/$H_2O$ (25 mL, 4:1, v:v) at rt was added p-TsOH (13 mg). The mixture was stirred at reflux for 12 h, cooled, concentrated under reduced pressure and adjusted to approx. pH 8 with aq. $NaHCO_3$. The mixture was extracted with EtOAc (3×20 mL) and the combined organic phase was washed with brine, dried over $Na_2SO_4$, concentrated and purified by silica gel chromatography to give intermediate (1R,5S)-7-((5-cyclopropyl-3-(2,6-dichlorophenyl)isoxazol-4-yl)methoxy)-3-oxabicyclo[3.3.1]nonan-9-one (2f).

Example 1: 2-((1R,5S,9S)-7-((5-Cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carboxylic acid

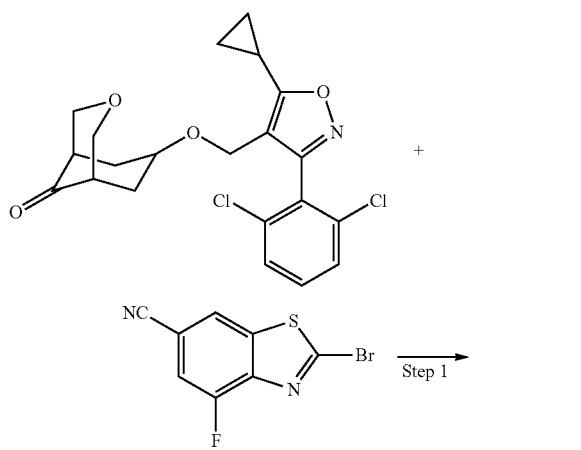

Example 1

Step 1: 2-((1R,5S,9S)-7-((5-Cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carbonitrile To a solution of (1R,5S)-7-((5-cyclopropyl-3-(2,6-dichlorophenyl)isoxazol-4-yl)methoxy)-3-oxabicyclo[3.3.1]nonan-9-one (2f, 120 mg, 0.28 mmol) and 4-bromo-3-fluoro-benzonitrile (1b, 73 mg, 0.28 mmol) in dry THF (20 mL) was cooled to −78° C., n-BuLi (0.28 mmol, 1.6M) was added dropwise. The mixture was stirred at −78° C. for 2 h and then quenched with sat. $NH_4Cl$ (30 mL) and extracted with EtOAc (3×50 mL). The combined organic layer was washed with brine (50 mL), dried over $Na_2SO_4$, concentrated and purified by silica-gel column chromatography (DCM/MeOH=30:1) to give title compound 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carbonitrile.

Step 2: 2-((1R,5S,9S)-7-((5-Cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carboxylic acid (Example 1)

To a solution of 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carbonitrile (100 mg, 0.18 mmol) in EtOH (10 mL) was added aq. NaOH (4N, 2 mL) and the mixture was stirred at 75° C. for 1 h, cooled, acidified by HCl (4M, 5 mL) and extracted with EtOAc (3×50 mL). The combined organic layer was washed with brine (50 mL), concentrated and purified by prep-HPLC to give the title compound 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carboxylic acid (Example 1).
$^1$H-NMR (500 MHz, DMSO-$d_6$): δ 13.44 (br s, 1H), 8.55 (d, J=1.0 Hz, 1H), 7.79 (dd, J=11.0, J=1.0 Hz, 1H), 6.66-7.56 (m, 3H), 6.44 (br s, 1H), 4.24 (s, 2H), 3.77-3.74 (m, 1H), 3.70 (d, J=11.0 Hz, 2H), 3.54 (d, J=11.0 Hz, 2H), 2.50-2.67 (m, 5H), 1.52 (dd, J=13.5, J=4.0 Hz, 2H), 1.17-1.09 (m, 4H). LC/MS (ESI): m/z 619.1 (M+H)$^+$.

Example 2: 2-((1R,5S,9S)-7-((5-Cyclopropyl-3-(2,6-dichlorophenyl)isoxazol-4-yl)methoxy)-9-hydroxy-3-oxabicyclo[3.3.1]nonan-9-yl)benzo[d]thiazole-6-carboxylic acid

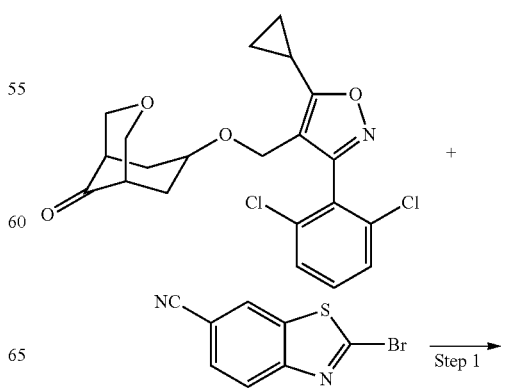

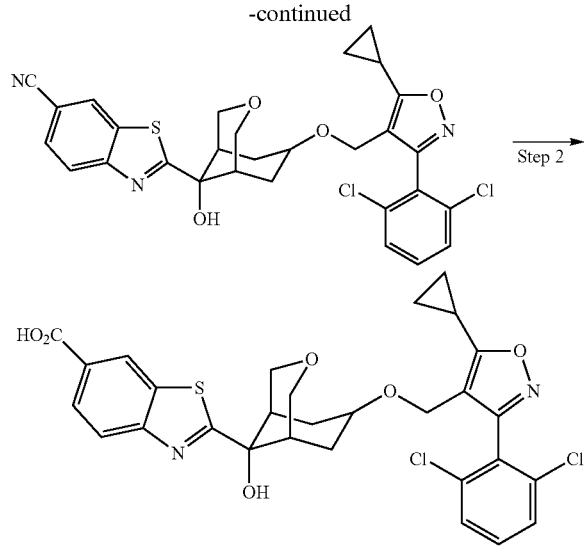

Example 2

Step 1: 2-((1R,5S,9s)-7-((5-cyclopropyl-3-(2,6-dichlorophenyl)isoxazol-4-yl)methoxy)-9-hydroxy-3-oxabicyclo[3.3.1]nonan-9-yl)benzo[d]thiazole-6-carbonitrile To a solution of (1R,5S)-7-((5-cyclopropyl-3-(2,6-dichlorophenyl)isoxazol-4-yl)methoxy)-3-oxabicyclo[3.3.1]nonan-9-one (2f, 120 mg, 0.28 mmol) and 2-bromo-benzo[d]thiazole-6-carbonitrile (70 mg, 0.28 mmol) in dry THF (20 mL) was cooled to −78° C., n-BuLi (0.28 mmol, 1.6M) was added dropwise. The mixture was stirred at −78° C. for 2 h and then quenched with sat. NH$_4$Cl (30 mL) and extracted with EtOAc (3×50 mL). The combined organic layer was washed with brine (50 mL), dried over Na$_2$SO$_4$, concentrated and purified by silica-gel column chromatography (DCM/MeOH=30:1) to give 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)benzo[d]thiazole-6-carbonitrile.

Step 2: 2-((1R,5S,9s)-7-((5-Cyclopropyl-3-(2,6-dichlorophenyl)isoxazol-4-yl)methoxy)-9-hydroxy-3-oxabicyclo[3.3.1]nonan-9-yl)benzo[d]thiazole-6-carboxylic acid (Example 2)

To a solution of 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)benzo[d]thiazole-6-carbonitrile (100 mg, 0.18 mmol) in EtOH (10 mL) was added aq. NaOH (4N, 2 mL) and the mixture was stirred at 75° C. for 1 h, cooled, acidified by HCl (4M, 5 mL) and extracted with EtOAc (3×50 mL). The combined organic layer was washed with brine (50 mL), concentrated and purified by prep-HPLC to give the title compound 2-((1R,5S,9S)-7-((5-cyclopropyl-3-(2,6-dichlorophenyl)isoxazol-4-yl)methoxy)-9-hydroxy-3-oxabicyclo[3.3.1]nonan-9-yl)benzo[d]thiazole-6-carboxylic acid (Example 2). $^1$H-NMR (500 MHz, DMSO-d$_6$): $^1$HNMR (500 MHz, DMSO-d$_6$): δ 13.15 (br s, 1H), 8.72 (s, 1H), 8.07-8.03 (m, 2H), 7.66-7.56 (m, 3H), 6.40 (br s, 1H), 4.24 (s, 2H), 3.79-3.75 (m, 1H), 3.68 (d, J=11.0 Hz, 2H), 3.53 (d, J=11.0 Hz, 2H), 2.43-2.26 (m, 5H), 1.51 (dd, J=13.5, J=4.0 Hz, 2H), 1.16-1.09 (m, 4H). LCMS (ESI): m/z 600.8 (M+H)$^+$.

Example 3: FRET Activity Assay

Determination of a ligand mediated cofactor peptide interaction to quantify ligand binding to the nuclear receptor FXR was performed as follows: Preparation of human FXR alpha ligand binding domain: The human FXRalpha LBD was expressed in *E. coli* strain BL21(DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of OD$_{600}$=0.4-0.6. Gene expression was then induced by addition of 0.5 mM IPTG. Cells were incubated an additional 6 h at 30° C., 180 rpm. Cells were collected by centrifugation (7000×g, 7 min, rt). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000×g, 15 sec, 4° C.) and washed twice in wash buffer (25 mM Tris, 50 mM KCl, 4 mM MgCl$_2$ and IM NaCl). The pellet was resuspended in 3 mL elution buffer per liter of original culture (elution buffer: 20 mM Tris, 60 mM KCl, 5 mM MgCl$_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM MgCl$_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B-CPSSHSSLTERHKILHRLLQEGSPS-COOH (SEQ ID NO: 1) where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 µL in a 384 well plate, in a Tris-based buffer (20 mM Tris-HCl pH 7.5; 60 mM KCl, 5 mM MgCl$_2$; 35 ng/µL BSA), containing 20-60 ng/well recombinantly expressed FXR-LBD fused to GST, 200-600 nM N-terminally biotinylated peptide, representing SRC1 aminoacids 676-700, 200 ng/well Streptavidin-x1APC conjugate (Prozyme) and 6-10 ng/well Eu W1024-antiGST (Perkin Elmer). DMSO content of the samples was kept at 1%. After generation of the assay mix and diluting the potentially FXR modulating ligands, the assay was equilibrated for 1 h in the dark at rt in FIA-plates black 384 well (Greiner). The LANCE signal was detected by a Perkin Elmer VICTOR2VTM Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the agonistic potential of the compounds, $EC_{50}$ values were determined for example compounds as listed below in Table 2 (FRET $EC_{50}$).

Example 4: Mammalian One Hybrid (M1H) Assay

Determination of a ligand mediated Gal4 promoter driven transactivation to quantify ligand binding mediated activation of FXR was performed as follows: The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the Photinus pyralis (American firefly) luciferase gene as the reporter gene. In order to improve experimental accuracy the plasmid pRL-CMV (Promega) was cotransfected. pRL-CMV contains the constitutive CMV promoter, controlling the expression of the *Renilla reniformis* luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicilin/Streptavidin per mL at 37° C. in 5% $CO_2$. Medium and supplements were obtained from Invitrogen. For the assay, $5 \times 10^5$ cells were plated per well in 96 well plates in 100 μL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicilin/Streptavidin per mL, incubated at 37° C. in 5% $CO_2$. The following day the cells were >90% confluence. Medium was removed and cells were transiently transfected using 20 μL per well of a OptiMEM-polyethylene-imine-based transfection-reagent (OptiMEM, Invitrogen; Polyethyleneimine, Aldrich Cat No. 40,827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and *renilla luciferase* activities were measured sequentially in the same cell extract using a Dual-Light-Luciferase-Assay system (Dyer et al., Anal. Biochem. 2000, 282, 158-161). All experiments were done in triplicates.

To assess the FXR agonistic potency of the example compounds, potency was determined in the M1H assay as listed below in Table 2 (M1H $EC_{50}$).

TABLE 2

| Example | FRET $IC_{50}$ (nM) | M1H $EC_{50}$ (nM) |
| --- | --- | --- |
| 1 | 19 | 216 |
| 2 | 30 | 175 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound selected from:

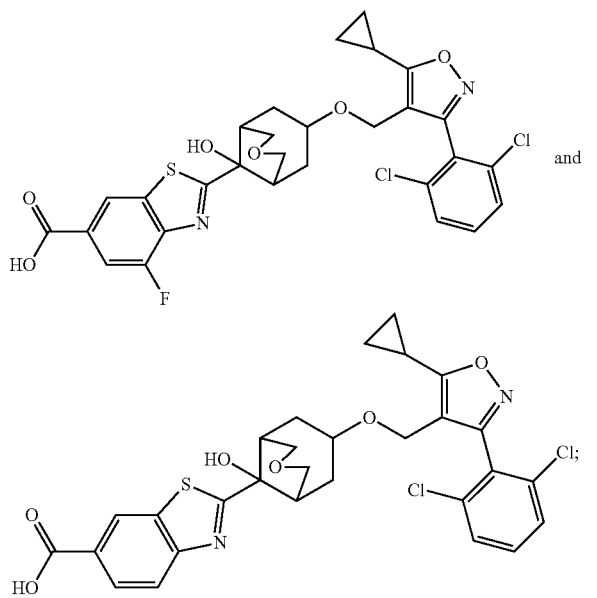

or a pharmaceutically acceptable salt, a stereoisomer, a mixture of stereoisomers, or a tautomer thereof.

2. The compound of claim 1 of the formula:

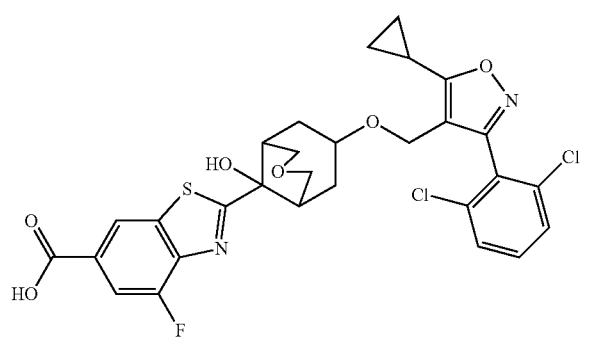 [SMILES: O=C(O)c1cc(F)c2nc(C3(O)C4COCC3CC(OCc3c(-c5c(Cl)cccc5Cl)noc3C3CC3)C4)sc2c1]

or a pharmaceutically acceptable salt, a stereoisomer, a mixture of stereoisomers, or a tautomer thereof.

3. The compound of claim 1 of the formula:

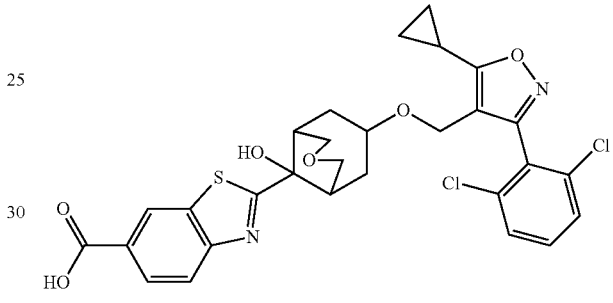

or a pharmaceutically acceptable salt, a stereoisomer, a mixture of stereoisomers, or a tautomer thereof.

4. A pharmaceutical composition comprising a compound of claim 1, or a pharmaceutically acceptable salt, a stereoisomer, a mixture of stereoisomers, or a tautomer thereof, and a pharmaceutically acceptable excipient.

5. A method of treating a condition selected from the group consisting of liver fibrosis, liver cirrhosis, liver steatosis, acute liver failure, Non-Alcoholic Fatty Liver Disease (NAFLD), Non-Alcoholic Steatohepatitis (NASH), Primary Biliary Cirrhosis (PBC), and Primary Sclerosing Cholangitis (PSC) comprising administering a compound of claim 1, or a pharmaceutically acceptable salt, a stereoisomer, a mixture of stereoisomers, or a tautomer thereof, to a patient in need thereof.

6. The method according to claim 5, wherein the condition is Non-Alcoholic Steatohepatitis (NASH).

* * * * *